US008032205B2

(12) United States Patent
Mullani

(10) Patent No.: US 8,032,205 B2
(45) Date of Patent: Oct. 4, 2011

(54) TRANSILLUMINATOR LIGHT SHIELD

(76) Inventor: Nizar A. Mullani, Sugar Land, TX (US)

( * ) Notice: Subject to any disclaimer, the term of this patent is extended or adjusted under 35 U.S.C. 154(b) by 1181 days.

(21) Appl. No.: 11/227,195

(22) Filed: Sep. 16, 2005

(65) Prior Publication Data

US 2007/0063150 A1    Mar. 22, 2007

(51) Int. Cl.
*A61B 6/00*    (2006.01)
(52) U.S. Cl. ........................................ 600/476
(58) Field of Classification Search ............... 600/473, 600/476, 477, 478, 407; 356/36, 369, 798; 606/9
See application file for complete search history.

(56) References Cited

U.S. PATENT DOCUMENTS

| 2,592,539 | A | * | 4/1952 | Cahill | 493/383 |
| 3,679,891 | A | * | 7/1972 | Quack | 362/309 |
| 4,913,132 | A | * | 4/1990 | Gabriel | 600/200 |
| 5,146,923 | A | * | 9/1992 | Dhawan | 600/476 |
| D391,006 | S | * | 2/1998 | Yang | D26/118 |
| 6,384,988 | B1 | * | 5/2002 | Muller et al. | 359/798 |
| 6,668,187 | B1 | | 12/2003 | Porath | |
| 7,006,223 | B2 | * | 2/2006 | Mullani | 356/369 |

* cited by examiner

*Primary Examiner* — Tse Chen
*Assistant Examiner* — Elmer Chao
(74) *Attorney, Agent, or Firm* — Welsh Flaxman & Gitler LLC

(57) ABSTRACT

Transillumination uses light to image tissues and organs, specifically the veins within the tissue. Strong ambient light hinders the imaging of veins and often, transillumination must be done in a dark or dim room. To enhance the capabilities of a transilluminator, a light shield is placed over the viewing area of the transilluminator so that turning off or dimming of ambient light is not necessary. For pediatric care, a frustroconical adapter attached to the bottom of the transilluminator. The adapter reduces the size of the viewing area.

5 Claims, 3 Drawing Sheets

TRANSILLUMINATOR LIGHT SHIELD

BACKGROUND OF THE INVENTION

Transillumination entails shining of a light through a body cavity or organ for diagnostic purposes. Typically, transillumination is performed in a room where the lights have been dimmed or turned off to facilitate the viewing of the part being studied. A bright light is pointed at the cavity or organ and due to the slight translucence of the part under consideration, some of the light passes through the part or organ. This test is often performed on newborns or infants with hydrocephalus or males suspected of having hydrocele. In addition, for tests performed on breast tissue to detect lesions and/or cysts. In newborns, the test is used to transilluminate the chest cavity if pneumothorax is suspected. Only in newborns is transillumination of the chest possible. Transillumination is painless and quickly performed with inexpensive equipment.

Classic mode of transillumination shines light in order to see internal details of the object. Another form of transillumination is side transillumination. In side transillumination, light shines from the side of the object to form a virtual light source below the skin. The light source moves with the device and allows transillumination of any part of the body up to a depth of about 6 mm. The side transillumination method is described in U.S. Pat. No. 5,146,923.

It is beneficial to shield the area viewed during transillumination from ambient light. U.S. Pat. No. 6,668,187 (Porath) discloses a transillumination mammography device having a pair of light shields positioned to shield detectors from ambient light.

It is an object of the invention to provide a dome shaped light shield for a transillumination device.

It is another object of the invention to provide a transilluminator providing imaging regardless of ambient light.

It is yet another object of the invention to provide a light shield for a transilluminator that is removable.

It is another object of the invention to provide a light shield for a transilluminator that is inexpensive to manufacture and easy to install on an existing transilluminator.

These and other objects of the invention will become apparent to one of ordinary skill in the art after reading the disclosure of the invention.

SUMMARY OF THE INVENTION

Transillumination uses light to image tissues and organs, specifically the veins within the tissue. Strong ambient light hinders the imaging of veins and often, transillumination must be done in a dark or dim room. To enhance the capabilities of a transilluminator, a light shield is placed over the viewing area of the transilluminator so that turning off or dimming of ambient light is not necessary. For pediatric care, a frustroconical adapter attached to the bottom of the transilluminator. The adapter reduces the size of the viewing area.

DETAILED DESCRIPTION OF THE INVENTION

Figure 1:
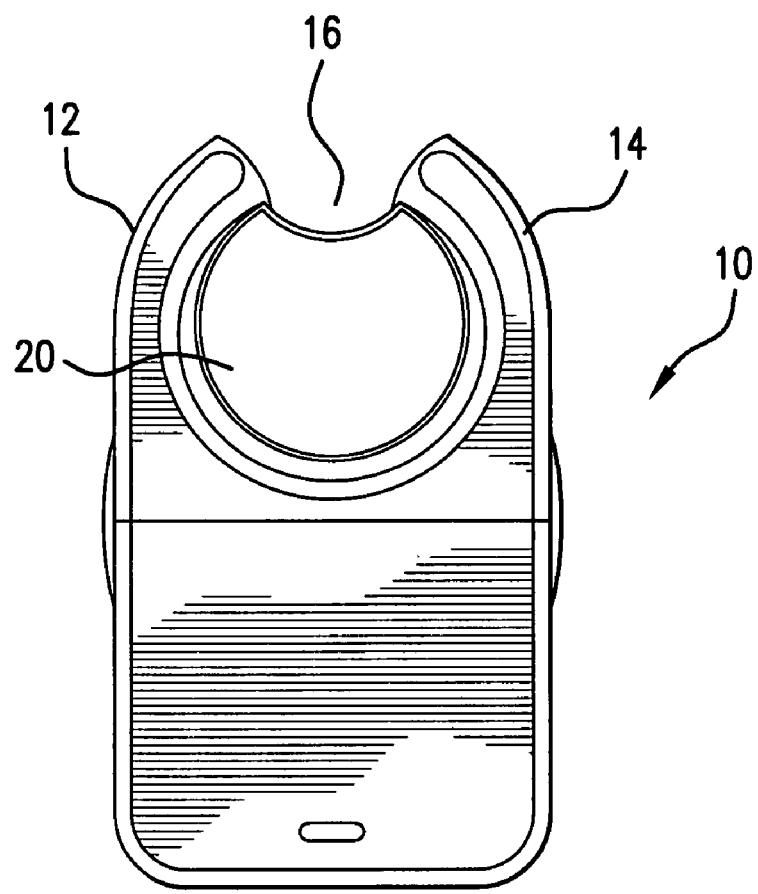
FIG. 1 is a top view of a transillumination device.
Figure 2:
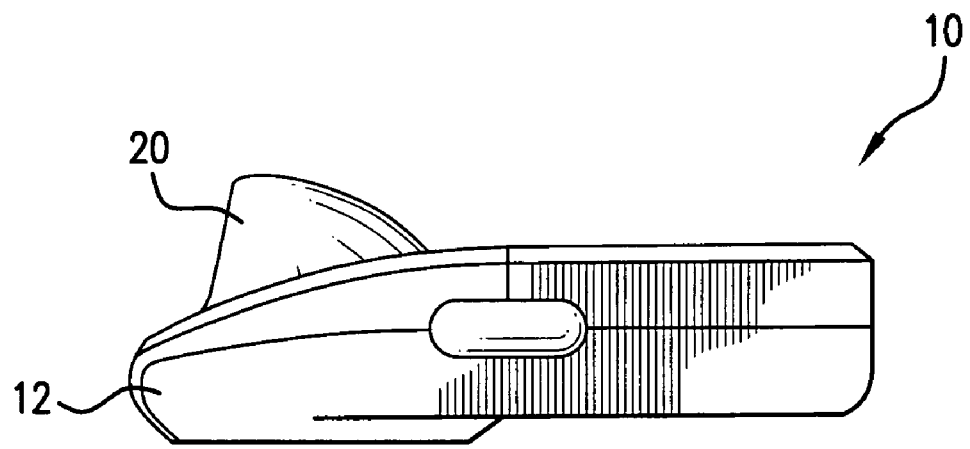
FIG. 2 is the side view of a transillumination device having a light shield.

The top view of a hand-held transilluminator 10 is seen in FIG. 1. The front is formed by a circular area of illumination 12 with a cut out to allow for vein access. The circular area of illumination forms a viewing area 16. Surrounding the viewing area, on the bottom surface, is a light source. The device is placed over the area to be viewed and the light provides transillumination for viewing. FIG. 2 shows the side view of a transilluminator having a light shield 20. The light shield has a dome like projection over the top surface of the transilluminator, blocking ambient light but allowing the user to still view the viewing area 16. The transillumination can also be a circular area of illumination connected to a housing, providing a power source, by a cable.

Figure 3:
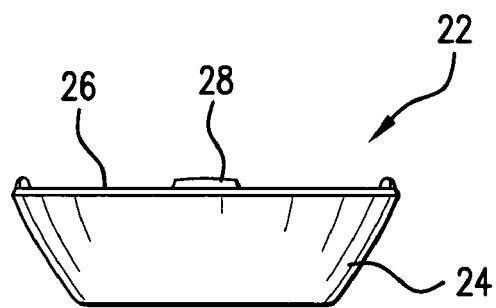
FIG. 3 is a rear view of the lower shield.
Figure 4:
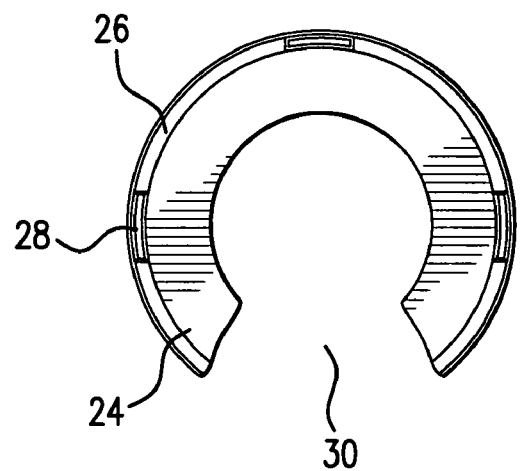
FIG. 4 is a top view of the lower shield.

FIG. 3 shows the rear view of the lower light shield 22. The lower light shield has a frustro conical sidewall 24 with a larger top edge 26. Several tabs 28 rise from the top edge for connection to the upper shield, as will be seen later. FIG. 4 is a top view of the lower light shield and an opening 30 in the front is seen. This opening corresponds to the cut out in the circular area of illumination 12 as the edges of the opening 30 substantially align with the cut out 14.

Figure 5:
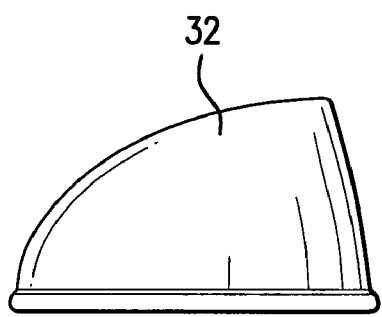
FIG. 5 is a side view of the upper shield.
Figure 6:
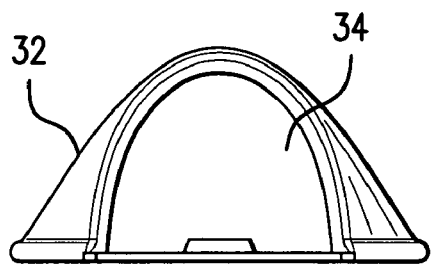
FIG. 6 is a front view of the upper shield.

FIG. 5 shows a side view of the upper light shield 32. The light shield has a truncated quarter hemisphere shape forming a dome like structure to block ambient light. The front view of the upper light shield is seen in FIG. 6 with the viewing aperture 34 clearly seen. The bottom edge of the viewing aperture substantially aligns with the top of opening 30 in the lower light shield.

Figure 7:
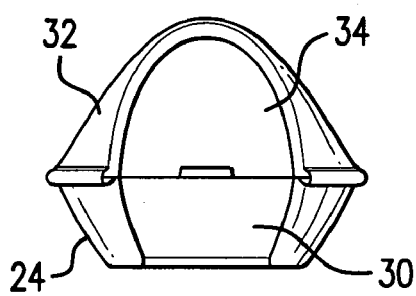
FIG. 7 is a front view of the upper and lower shields connected.
Figure 8:
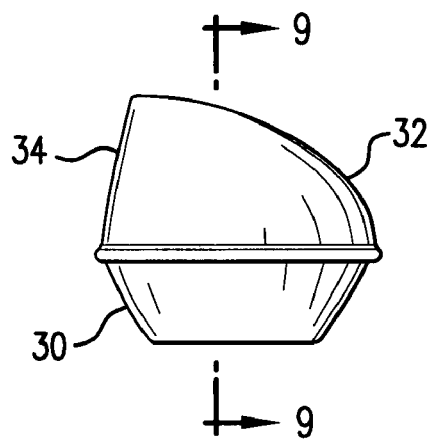
FIG. 8 is a side view of the upper and lower shields connected.

The relationship between the upper light shield is seen clearly in FIG. 7, with the top edge of the opening 30 substantially aligned with the bottom edge of the viewing opening 34. The bottom edge of the upper light shield has a flange 36 overlapping the top edge of the lower shield to maintain the two in contact. The side view of the connected light shield is depicted in FIG. 8. The sidewall of the lower light shield is surrounded by the circular area of illumination with the dome of the upper shield rising above the top surface of the transilluminator, as was seen in FIG. 2.

Figure 9:
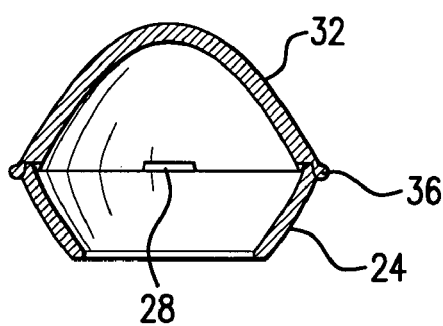
FIG. 9 is a cross sectional view of the upper and lower shields along line 9-9 of FIG. 8.

FIG. 9 shows the cross section through line 9-9 of FIG. 8 and clearly demonstrates the relationship between the two parts of the light shield.

Figure 10:
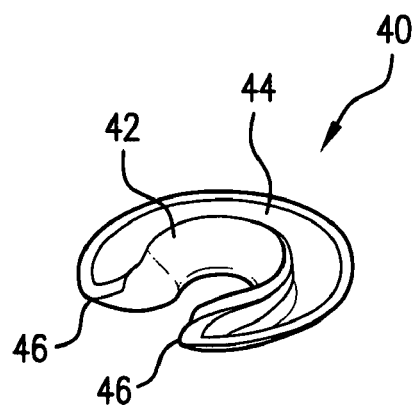
FIG. 10 is a perspective view of a transilluminator mini adapter.

A mini adapter is shown in FIG. 10. The mini adapter 40 connects to the bottom of the transilluminator. The mini adapter has a frustro conical shape with a smaller bottom edge and serves to reduce the viewing area to a smaller diameter. Mini adapters are particularly useful in pediatric care. The mini adapter is formed by an inner sidewall 42 and outer sidewall 44 connected to one another by bridge 46.

Figure 11:
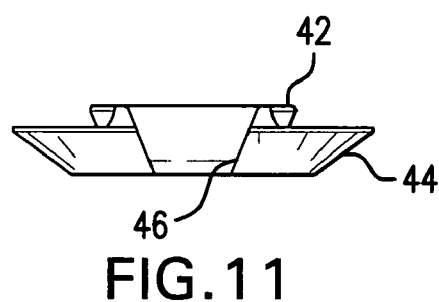
FIG. 11 is a front view of the light shield mini adapter.
Figure 12:
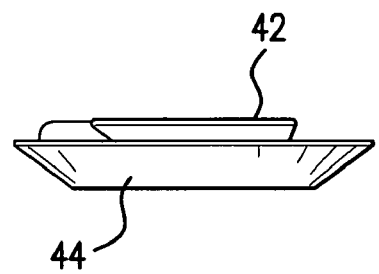
FIG. 12 is a side view of the light shield mini adapter.

FIG. 11 shows the front view of the mini adapter. The frustro conical shape of the outer wall 44 is clearly seen along with the fact that the inner wall 42 has a greater height than the outer wall 44. The side view of FIG. 12 shows the relationship between the inner and outer wall more clearly.

While the invention has been disclosed with reference to preferred embodiments, variations and modifications would be apparent to one of ordinary skill in the art. The invention encompasses such variations and modifications.

What is claimed is:

1. A transillumination device to image veins within tissue, comprising
  a housing to be grasped by a user during use of said transillumination device, said housing having a top surface and a bottom surface;
  a light source in said housing provided on said bottom surface, surrounding a viewing area;
  the viewing area illuminated by said light source;
  a dome-shaped upper light shield having an upper surface and a viewing aperture extending above said top surface of the housing and over said viewing area, said upper light shield blocking ambient light above the viewing area but allowing the user to image veins within tissue;
  a lower light shield in direct contact with said upper light shield, said lower light shield provided around said light source and said viewing area; and
  an adapter depending from said bottom surface of said housing, said adapter being frusto conical and further wherein said adapter reduces the size of the viewing area.

2. The transillumination device of claim 1, wherein said lower light shield is frustro conical.

3. The transillumination device of claim 1, wherein said adapter comprises a first inner wall, a second outer wall and a bridge extending between said first inner and second outer wall.

4. The transillumination device in accordance with claim 1, wherein said upper light shield is removable.

5. The transillumination device in accordance with claim 1, wherein said upper light shield is provided with a flange overlapping a top edge of said lower light shield.

* * * * *